(12) United States Patent
Terrill et al.

(10) Patent No.: US 10,245,085 B2
(45) Date of Patent: *Apr. 2, 2019

(54) BONE PLATE WITH A TRANSFIXATION SCREW HOLE

(71) Applicant: OsteoMed LLC, Addison, TX (US)

(72) Inventors: Lance Nathan Terrill, Dallas, TX (US); Bruce R. Werber, Scottsdale, AZ (US)

(73) Assignee: OsteoMed LLC, Addison, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/707,891

(22) Filed: Sep. 18, 2017

(65) Prior Publication Data

US 2018/0000529 A1 Jan. 4, 2018

Related U.S. Application Data

(63) Continuation of application No. 15/147,828, filed on May 5, 2016, now Pat. No. 9,763,716, which is a (Continued)

(51) Int. Cl.
*A61B 17/80* (2006.01)
*A61B 17/88* (2006.01)
*A61B 17/84* (2006.01)

(52) U.S. Cl.
CPC ...... *A61B 17/8057* (2013.01); *A61B 17/8061* (2013.01); *A61B 17/88* (2013.01);
(Continued)

(58) Field of Classification Search
CPC ................. A61B 17/8014; A61B 17/8061
See application file for complete search history.

(56) References Cited

U.S. PATENT DOCUMENTS

| 1,025,008 A | 4/1912 | Miner |
|---|---|---|
| 1,105,105 A | 7/1914 | Sherman |

(Continued)

FOREIGN PATENT DOCUMENTS

| EP | 1468655 A2 | 10/2004 |
|---|---|---|
| EP | 1897509 A1 | 9/2007 |

(Continued)

OTHER PUBLICATIONS

Arthrex, "Midfoot Plating Techniques," Surgical Techniques, 2007, 12 pages.

(Continued)

*Primary Examiner* — Nicholas W Woodall
(74) *Attorney, Agent, or Firm* — Norton Ross Fulbright US LLP

(57) ABSTRACT

A system for securing bones together across a joint includes a transfixation screw and a plate. The plate includes an elongate spine having a transfixation screw hole disposed along the spine. The transfixation screw hole includes an inner surface configured to direct the transfixation screw through the transfixation screw hole such that the transfixation screw extends alongside the bridge portion at a trajectory configured to pass through a first position on the first bone and a second position on the second bone once the plate is placed across the joint. The transfixation screw includes a head configured to abut the inner surface of the transfixation screw hole and a shaft configured to contiguously extend through the first bone, across the joint, and into the second bone.

9 Claims, 3 Drawing Sheets

Related U.S. Application Data continuation of application No. 14/015,900, filed on Aug. 30, 2013, now Pat. No. 9,351,776, which is a continuation of application No. 12/431,017, filed on Apr. 28, 2009, now Pat. No. 8,529,608.

(52) U.S. Cl.
CPC ......... *A61B 17/809* (2013.01); *A61B 17/8014* (2013.01); *A61B 17/8052* (2013.01); *A61B 17/8085* (2013.01); *A61B 17/848* (2013.01)

(56) References Cited

U.S. PATENT DOCUMENTS

| | | | |
|---|---|---|---|
| 1,869,726 | A | 8/1932 | Youngren |
| 2,133,859 | A | 10/1938 | Hawley |
| 2,398,915 | A | 4/1946 | Bell |
| 2,443,363 | A | 6/1948 | Townsend et al. |
| 2,489,870 | A | 11/1949 | Dzus |
| 2,501,978 | A | 3/1950 | Wichman |
| 2,561,550 | A | 7/1951 | Wright |
| 2,737,835 | A | 3/1956 | Herz |
| 3,463,148 | A | 8/1969 | Treace |
| 3,534,731 | A | 10/1970 | Muller |
| 3,552,389 | A | 1/1971 | Allgower et al. |
| 3,593,709 | A | 7/1971 | Halloran |
| 3,668,972 | A | 6/1972 | Allgower et al. |
| 3,695,259 | A | 10/1972 | Yost |
| 3,716,050 | A | 2/1973 | Johnston |
| 3,741,205 | A | 6/1973 | Markolf et al. |
| 3,779,240 | A | 12/1973 | Kondo |
| 3,807,394 | A | 4/1974 | Attenborough |
| 4,219,015 | A | 8/1980 | Steinemann |
| 4,338,921 | A | 7/1982 | Harder et al. |
| 4,338,926 | A | 7/1982 | Kummer et al. |
| 4,364,382 | A | 12/1982 | Mennen |
| 4,408,601 | A | 10/1983 | Wenk |
| 4,484,570 | A | 11/1984 | Sutter et al. |
| 4,488,543 | A | 12/1984 | Tomier |
| 4,493,317 | A | 1/1985 | Klaue |
| 4,503,848 | A | 3/1985 | Caspar et al. |
| 4,513,744 | A | 4/1985 | Klaue |
| 4,565,193 | A | 1/1986 | Streli |
| 4,573,458 | A | 3/1986 | Lower |
| 4,651,724 | A | 3/1987 | Berentey et al. |
| 4,683,878 | A | 8/1987 | Carter |
| 4,794,918 | A | 1/1989 | Wolter |
| 4,800,874 | A | 1/1989 | David et al. |
| 4,838,252 | A | 6/1989 | Klaue |
| 4,867,144 | A | 9/1989 | Karas et al. |
| 4,955,886 | A | 9/1990 | Pawluk |
| 4,959,065 | A | 9/1990 | Arnett et al. |
| 5,002,544 | A | 3/1991 | Klaue et al. |
| 5,006,120 | A | 4/1991 | Carter |
| 5,015,249 | A | 5/1991 | Nakao et al. |
| 5,021,056 | A | 6/1991 | Hoffmann et al. |
| 5,041,113 | A | 8/1991 | Biedermann et al. |
| 5,053,036 | A | 10/1991 | Perren et al. |
| 5,053,039 | A | 10/1991 | Hofmann et al. |
| 5,057,111 | A | 10/1991 | Park |
| 5,085,660 | A | 2/1992 | Lin |
| 5,129,903 | A | 7/1992 | Luhr et al. |
| 5,151,103 | A | 9/1992 | Tepic et al. |
| 5,190,544 | A * | 3/1993 | Chapman ............... A61B 17/72 606/280 |
| 5,234,431 | A | 8/1993 | Keller |
| 5,269,784 | A | 12/1993 | Mast |
| 5,304,180 | A | 4/1994 | Slocum |
| 5,330,535 | A | 7/1994 | Moser et al. |
| 5,344,421 | A | 9/1994 | Crook |
| 5,380,327 | A | 1/1995 | Eggers et al. |
| 5,387,102 | A | 2/1995 | Wagner et al. |
| 5,443,467 | A | 8/1995 | Biedermann et al. |
| 5,474,553 | A | 12/1995 | Baumgart |
| 5,486,176 | A | 1/1996 | Hildebrand et al. |
| 5,487,741 | A | 1/1996 | Maruyama et al. |
| 5,501,684 | A | 3/1996 | Schlapfer et al. |
| 5,531,746 | A | 7/1996 | Errico et al. |
| 5,549,612 | A | 8/1996 | Yapp et al. |
| 5,578,034 | A | 11/1996 | Estes |
| 5,591,166 | A | 1/1997 | Bernhardt et al. |
| 5,601,553 | A | 2/1997 | Trebing et al. |
| 5,603,713 | A | 2/1997 | Aust et al. |
| 5,607,426 | A | 3/1997 | Ralph et al. |
| 5,607,428 | A | 3/1997 | Lin |
| 5,620,448 | A | 4/1997 | Puddu |
| 5,643,265 | A | 7/1997 | Errico et al. |
| 5,662,655 | A | 9/1997 | Laboureau et al. |
| 5,674,222 | A | 10/1997 | Berger et al. |
| 5,676,667 | A | 10/1997 | Hausman |
| 5,681,311 | A | 10/1997 | Foley et al. |
| 5,709,686 | A | 1/1998 | Talos et al. |
| 5,725,588 | A | 3/1998 | Errico et al. |
| 5,733,287 | A | 3/1998 | Tepic et al. |
| 5,735,853 | A | 4/1998 | Olerud |
| 5,741,258 | A | 4/1998 | Klaue et al. |
| 5,746,742 | A | 5/1998 | Runciman et al. |
| 5,749,872 | A | 5/1998 | Kyle et al. |
| 5,749,875 | A | 5/1998 | Puddu |
| 5,810,823 | A | 9/1998 | Klaue et al. |
| 5,931,838 | A | 8/1999 | Vito |
| 5,938,664 | A | 8/1999 | Winquist et al. |
| 5,951,558 | A | 9/1999 | Fiz |
| 5,954,722 | A | 9/1999 | Bono |
| 5,964,762 | A | 10/1999 | Biedermann et al. |
| 6,001,099 | A | 12/1999 | Huebner |
| 6,093,188 | A | 7/2000 | Murray |
| 6,117,173 | A | 9/2000 | Taddia et al. |
| 6,139,550 | A | 10/2000 | Michelson |
| 6,152,927 | A | 11/2000 | Farris et al. |
| 6,183,475 | B1 | 2/2001 | Lester et al. |
| 6,193,721 | B1 | 2/2001 | Michelson |
| 6,206,881 | B1 | 3/2001 | Frigg et al. |
| 6,224,602 | B1 | 5/2001 | Hayes |
| 6,228,085 | B1 | 5/2001 | Theken et al. |
| 6,235,032 | B1 | 5/2001 | Link |
| 6,235,033 | B1 | 5/2001 | Brace et al. |
| 6,235,034 | B1 | 5/2001 | Bray |
| 6,241,731 | B1 | 6/2001 | Fiz |
| 6,261,291 | B1 | 7/2001 | Talaber et al. |
| 6,302,883 | B1 | 10/2001 | Bono |
| 6,309,393 | B1 | 10/2001 | Tepic |
| 6,315,779 | B1 | 11/2001 | Morrison et al. |
| 6,322,562 | B1 | 11/2001 | Wolter |
| 6,342,055 | B1 | 1/2002 | Eisermann et al. |
| 6,348,052 | B1 | 2/2002 | Sammarco |
| 6,383,186 | B1 | 5/2002 | Michelson |
| 6,413,259 | B1 | 7/2002 | Lyons et al. |
| 6,454,770 | B1 | 9/2002 | Klaue |
| 6,503,250 | B2 | 1/2003 | Paul |
| 6,527,776 | B1 | 3/2003 | Michelson |
| 6,533,789 | B1 | 3/2003 | Hall, IV et al. |
| 6,575,975 | B2 | 6/2003 | Brace et al. |
| 6,579,975 | B1 | 6/2003 | Brace et al. |
| 6,595,993 | B2 | 7/2003 | Donno et al. |
| 6,602,255 | B1 | 8/2003 | Campbell et al. |
| 6,623,486 | B1 | 9/2003 | Weaver et al. |
| 6,669,701 | B2 | 12/2003 | Steiner et al. |
| 6,682,531 | B2 | 1/2004 | Winquist et al. |
| 6,695,846 | B2 | 2/2004 | Richelsoph et al. |
| 6,719,759 | B2 | 4/2004 | Wagner et al. |
| 6,755,832 | B2 | 6/2004 | Happonen et al. |
| 6,755,833 | B1 | 6/2004 | Paul et al. |
| 6,821,278 | B2 | 11/2004 | Frigg et al. |
| 6,890,334 | B2 | 5/2005 | Brace et al. |
| 6,945,973 | B2 | 9/2005 | Bray |
| 7,001,389 | B1 | 2/2006 | Navarro et al. |
| 7,128,744 | B2 | 10/2006 | Weaver et al. |
| 7,175,624 | B2 | 2/2007 | Konieczynski et al. |
| 7,179,260 | B2 | 2/2007 | Gerlach et al. |
| 7,273,481 | B2 | 9/2007 | Lombardo et al. |
| 7,288,095 | B2 | 10/2007 | Baynham et al. |
| 7,309,340 | B2 | 12/2007 | Fallin et al. |
| 7,311,712 | B2 | 12/2007 | Dalton |

(56) References Cited

U.S. PATENT DOCUMENTS

| | | |
|---|---|---|
| 7,331,961 B2 | 2/2008 | Abdou |
| 2001/0037112 A1 | 11/2001 | Brace et al. |
| 2002/0082606 A1 | 6/2002 | Suddaby |
| 2003/0040749 A1 | 2/2003 | Grabowski et al. |
| 2003/0078583 A1 | 4/2003 | Biedermann et al. |
| 2003/0187440 A1 | 10/2003 | Richelsoph et al. |
| 2003/0187442 A1 | 10/2003 | Richelsoph et al. |
| 2003/0199876 A1 | 10/2003 | Brace et al. |
| 2004/0015169 A1 | 1/2004 | Gause |
| 2004/0034354 A1 | 2/2004 | Paul |
| 2004/0059334 A1 | 3/2004 | Weaver et al. |
| 2004/0059335 A1 | 3/2004 | Weaver et al. |
| 2004/0087951 A1 | 5/2004 | Khalili |
| 2004/0127901 A1 | 7/2004 | Huebner et al. |
| 2005/0010226 A1 | 1/2005 | Grady et al. |
| 2005/0065521 A1 | 3/2005 | Steger et al. |
| 2005/0070904 A1 | 3/2005 | Gerlach et al. |
| 2005/0080421 A1 | 4/2005 | Weaver et al. |
| 2005/0131413 A1 | 6/2005 | O'Driscoll et al. |
| 2005/0234455 A1 | 10/2005 | Binder et al. |
| 2006/0015102 A1 | 1/2006 | Toullec et al. |
| 2006/0036249 A1 | 2/2006 | Baynham et al. |
| 2006/0173459 A1 | 8/2006 | Kay et al. |
| 2006/0233596 A1 | 10/2006 | Sanders et al. |
| 2006/0235396 A1 | 10/2006 | Sanders et al. |
| 2006/0235397 A1 | 10/2006 | Sanders et al. |
| 2006/0241592 A1 | 10/2006 | Myerson et al. |
| 2006/0241607 A1 | 10/2006 | Myerson et al. |
| 2006/0241608 A1 | 10/2006 | Myerson et al. |
| 2007/0055253 A1 | 3/2007 | Orbay et al. |
| 2007/0088360 A1 | 4/2007 | Orbay et al. |
| 2007/0123880 A1 | 5/2007 | Medoff |
| 2007/0213880 A1 | 5/2007 | Medoff |
| 2007/0162020 A1 | 7/2007 | Gerlach et al. |
| 2007/0233106 A1* | 10/2007 | Horan ................ A61B 17/8061 606/282 |
| 2007/0233115 A1 | 10/2007 | Sixto et al. |
| 2007/0239163 A1 | 10/2007 | Strnad et al. |
| 2007/0260244 A1 | 11/2007 | Wolter |
| 2007/0270850 A1* | 11/2007 | Geissler ................ A61B 17/15 606/326 |
| 2007/0276383 A1 | 11/2007 | Rayhack |
| 2007/0276386 A1 | 11/2007 | Gerlach et al. |
| 2008/0015591 A1 | 1/2008 | Castaneda et al. |
| 2008/0015592 A1 | 1/2008 | Long et al. |

FOREIGN PATENT DOCUMENTS

| | | |
|---|---|---|
| JP | 2007-500069 A | 1/2007 |
| WO | WO-2007/131287 A1 | 11/2007 |

OTHER PUBLICATIONS

PCT Invitation to Pay Additional Fees and, Where Applicable, Protest Fee; International Applicaiton No. PCT/US2010/031328, International Filing Date Apr. 16, 2010.

PCT Notification of Transmittal of the International Search Report and the Written Opinion of the International Searching Authority, or the Declaration; International Application No. PCT/US2010/031328; International Filing Date: Apr. 16, 2010.

Vergrugge, J., "An Improved Bone Clamp and a Plate for Internal Fixation of Fractures," J. Bone Joint Surg. Am., 1946, vol. 28, pp. 174-175.

Office Action issued for Japanese Patent Applicaiton No. 2012-508524, dated Dec. 3, 2013, 10 pages with English language translation.

* cited by examiner

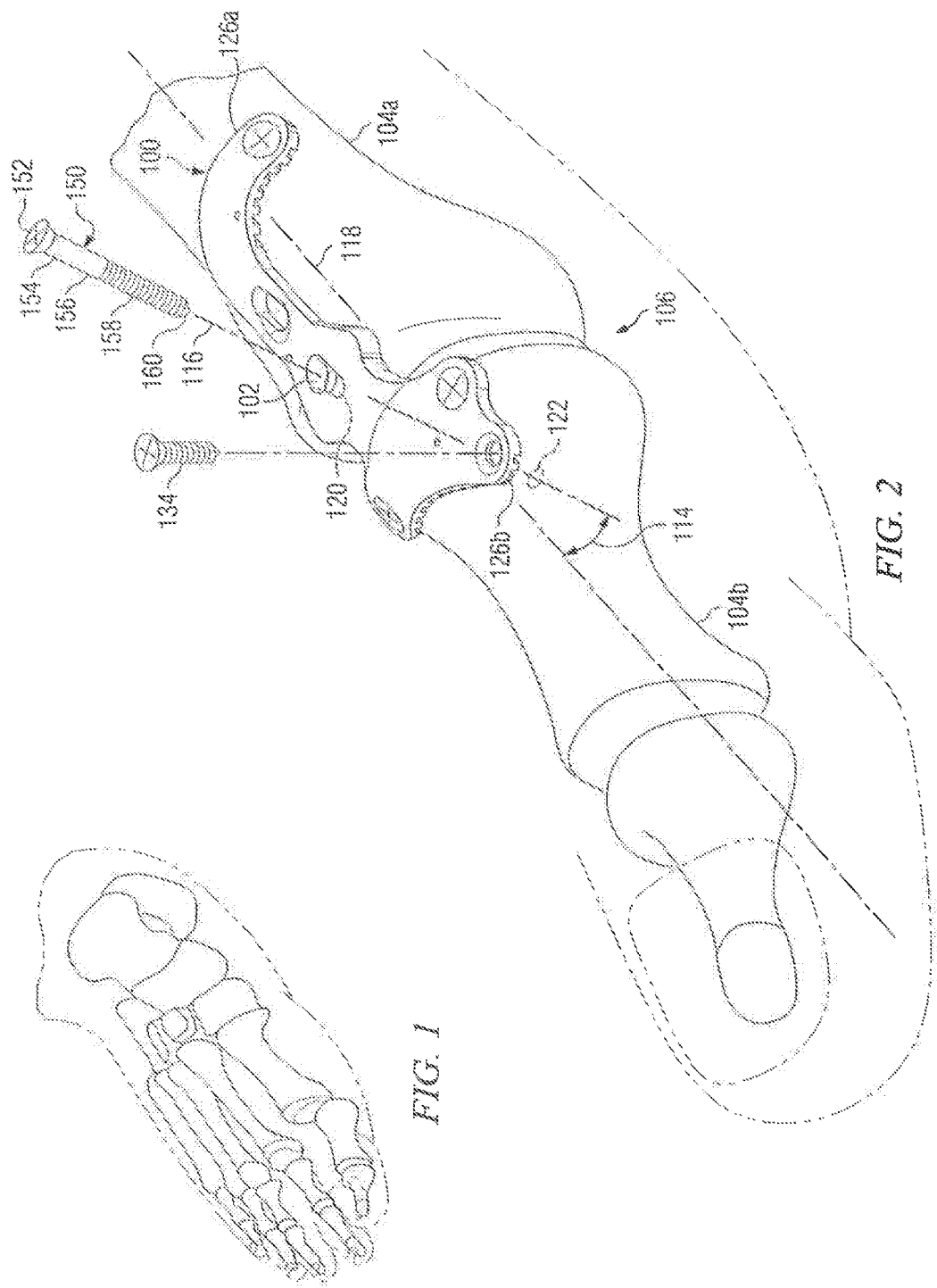

BONE PLATE WITH A TRANSFIXATION SCREW HOLE

CROSS-REFERENCE TO RELATED APPLICATIONS

The present application is a continuation of co-pending, commonly assigned, patent application Ser. No. 15/147,828 entitled "BONE PLATE WITH A TRANSFIXATION SCREW HOLE," filed May 5, 2016, which is a continuation of patent application Ser. No. 14/015,900 entitled "BONE PLATE WITH A TRANSFIXATION SCREW HOLE," filed Aug. 30, 2013, which is a continuation of patent application Ser. No. 12/431,017 entitled "BONE PLATE WITH A TRANSFIXATION SCREW HOLE," filed Apr. 28, 2009, U.S. Pat. No. 8,529,608, issued Sep. 10, 2013, the disclosures of which are hereby incorporated herein by reference in their entirety.

TECHNICAL FIELD

The present disclosure relates to a device for securing bones together, and more particularly, to a bone plate with a transfixation screw hole.

BACKGROUND OF THE INVENTION

When performing certain medical procedures, such as reconstructing a joint that has been damaged due to bone or soft tissue trauma, a surgeon may need to fuse the bones of the joint together in a configuration that approximates the natural geometry of the joint. One way to achieve this objective is to attach the bones of the joint to a plate that holds the bones in alignment with one another while they fuse together.

BRIEF SUMMARY OF THE INVENTION

The present disclosure relates generally to orthopedic devices. More specifically, the present disclosure relates to a bone plate with a transfixation screw hole for securing the bones of a joint together and a method for using the same.

In particular embodiments, a system for securing bones together across a joint includes a transfixation screw and a plate. The plate includes an elongate spine having a first end that includes at least one attachment point for attaching the first end to a first bone on a first side of a joint, a second end that includes at least one attachment point for attaching the second end to a second bone on a second side of the joint, and a bridge portion disposed between the first end and the second end configured to span across the joint. The plate further includes a transfixation screw hole disposed along the spine. The transfixation screw hole includes an inner surface configured to direct the transfixation screw through the transfixation screw hole such that the transfixation screw extends alongside the bridge portion at a trajectory configured to pass through a first position on the first bone and a second position on the second bone once the plate is placed across the joint. The transfixation screw comprises a head configured to abut the inner surface of the transfixation screw hole and a shaft configured to contiguously extend through the first bone, across the joint, and into the second bone.

Depending upon design, a central axis of the inner surface of the transfixation screw hole may define the trajectory, and the trajectory may be configured to cross a neutral bending axis of the joint once the plate is placed across the joint.

In particular embodiments, a plate for securing bones together may include an elongate spine having a first end that includes at least one attachment point for attaching the first end to a first bone on a first side of a joint, a second end that includes at least one attachment point for attaching the second end to a second bone on a second side of the joint, and a bridge portion disposed between the first end and the second end configured to span across the joint. The plate may further include a transfixation screw hole disposed along the spine. The transfixation screw hole includes an inner surface configured to direct a transfixation screw through the transfixation screw hole such that the transfixation screw extends alongside the bridge portion at a trajectory configured to pass through a first position on the first bone and a second position on the second bone once the plate is placed across the joint.

In particular embodiments, a method for securing bones together across a joint includes placing a plate over a first bone on a first side of a joint and a second bone on a second side of the joint. The plate may include an elongate spine having a first end that includes at least one attachment point for attaching the first end to the first bone, a second end that includes at least one attachment point for attaching the second end to the second bone, and a bridge portion disposed between the first end and the second end configured to span across the joint. The plate may further include a transfixation screw hole disposed along the spine. The transfixation screw hole includes an inner surface configured to direct the transfixation screw through the transfixation screw hole such that the transfixation screw extends alongside the bridge portion at a trajectory configured to pass through a first position on the first bone and a second position on the second bone once the plate is placed across the joint. The method may further include attaching the plate to the first bone and the second bone, and inserting a transfixation screw into the first bone and the second bone through the transfixation screw hole. The transfixation screw may include a head configured to abut the inner surface of the transfixation screw hole and a shaft configured to contiguously extend through the first bone, across the joint, and into the second bone.

Particular embodiments of the present disclosure may provide a number of technical advantages, including for example, the ability to tightly couple the bones of a joint together by inserting a transfixation screw across the joint through a bone plate. In particular embodiments, the transfixation screw may have a "lag effect" that enables the bones of the joint to be approximated with one another by rotation of the transfixation screw. For example, the transfixation screw may include an unthreaded portion configured to rotate freely within the first bone and a threaded portion configured to threadably engage the second bone. When the transfixation screw is rotated, the unthreaded portion of the transfixation screw may rotate freely within the first bone while the threaded portion of the transfixation screw advances into the second bone, drawing the second bone toward the first bone and compressing the joint. These technical advantages (e.g., the presence of the transfixation screw across the joint, and the lag effect of the transfixation screw) may increase the contact pressure on the bony interface of the joint, increasing the probability of a positive fusion.

Depending upon design, the inner surface of the transfixation screw hole in the plate may direct the transfixation screw along a trajectory that crosses a neutral bending axis of the joint as the transfixation screw passes from the first bone to the second bone. This technical advantage may create a "tension band" construct that enables the transfixation screw to absorb a portion of the mechanical stress that would otherwise be imposed upon the plate above the joint when a load is applied to the joint. This technical advantage may enhance the integrity and reliability of the plate and increase the load that the plate may support without increasing plate thickness. Other technical advantages of the present disclosure will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

For a more complete understanding of the present disclosure and its advantages, reference is now made to the following descriptions, taken in conjunction with the accompanying drawings, in which:

FIG. 1 illustrates a failed metatarso-phalangeal joint in the big toe of a human foot;

FIG. 2 illustrates a bone plate being used in conjunction with a transfixation screw to repair the failed metatarso-phalangeal joint of FIG. 1 according to an example embodiment of the present disclosure;

DETAILED DESCRIPTION OF THE INVENTION

Figure 3:
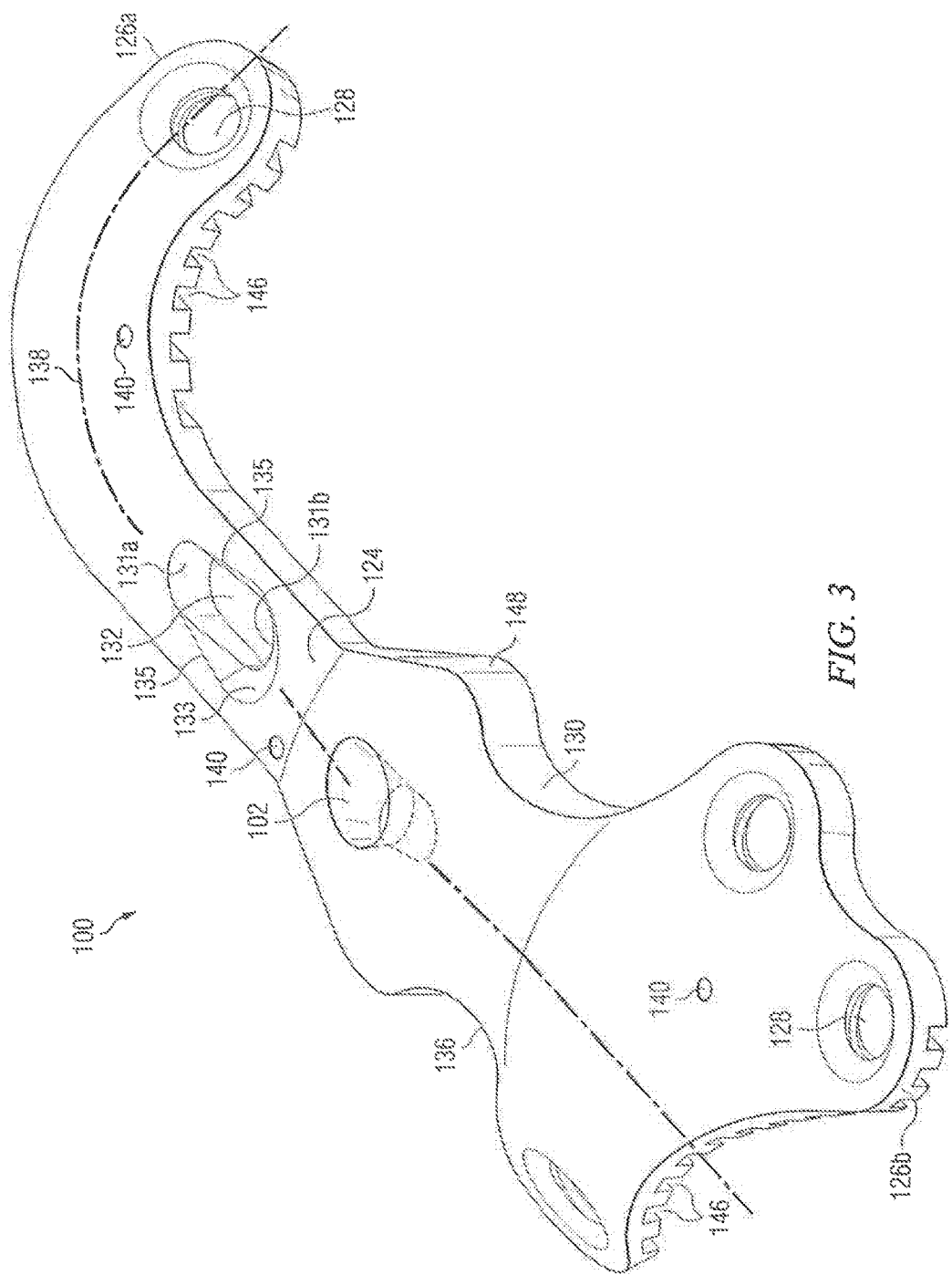
FIG. 3 illustrates a more detailed isometric view of the bone plate of FIG. 2.

The metatarso-phalangeal joint is a joint between a metatarsal bone of the foot and the proximal phalanx of a toe. It is common, particularly in sports, for the first metatarsophalangeal joint (e.g., the metatarso-phalangeal joint of the big toe) to be injured as a result of trauma to or hyper extension of the big toe. In other scenarios, degradation of the metatarsophalangeal joint may be caused by arthritis. Minor injuries to the metatarso-phalangeal joint, such as a sprain, may often be treated using conservative measures such as immobilization and icing of the toe, accompanied by rest and anti-inflammatory medication. These measures may be followed by taping or splinting of the injured joint to help prevent recurrent hyperextensions of the toe.

In more severe cases involving major trauma to the bone or soft tissue of the metatarso-phalangeal joint, as illustrated in FIG. 1, conservative measures may be ineffective, and surgery may be required. One procedure for reconstructing a severely damaged metatarso-phalangeal joint involves fusing the bones of the joint together using plates and/or screws. More particularly, a fusion procedure may involve reducing the opposing faces of the bones of the joint to a bleeding bone bed, approximating the bones with one another, and screwing the bones together to promote fusion. In some cases, the bones may be screwed together without the use of a plate. However, this option may not provide adequate lateral support for the bones, possibly allowing them to shift out of alignment, resulting in a malunion or a nonunion of the joint.

Another option for surgically repairing a severely damaged metatarso-phalangeal joint involves securing the bones of the joint together using a plate. In this procedure, after the bones of the joint have been approximated next to one another, the plate may be laid across the joint. The plate may then be screwed to the bones of the joint to hold them in alignment next to one another, enabling the joint fuse. However, when a load is placed upon the joint (e.g., when weight is placed upon the foot) it is possible for the plate to bend or break above the joint. This may cause the bones of the joint to fall out of approximation, resulting in a nonunion (e.g., a failed fusion of the joint). Consequently, the ability to rigidly hold the bones of a joint in tight approximation without bending or breaking is one metric for judging the effectiveness of a joint-fixation plate.

One way to increase the durability and reliability of a joint-fixation plate is to include a transfixation screw hole in the plate that enables a transfixation screw to transfix the joint through the plate. As explained in more detail below, once the transfixation screw is screwed across the joint, it may absorb some of the stress that would otherwise be exerted on the plate when a load is placed upon the joint. This may reduce the strain on the plate, increasing its reliability and durability. Additionally, while the plate may provide lateral support for the joint, the transfixation screw may hold the bones of the joint in tight approximation, increasing the likelihood of a positive fusion of the joint. This may be particularly important on the plantar side of the joint due to tensile stresses exerted on that side of the joint when loaded.

FIGS. 2-3 illustrate an example embodiment of a bone plate 100 that includes a transfixation screw hole 102 in accordance with the present disclosure. More particularly, FIG. 2 illustrates bone plate 100 being used in conjunction with a transfixation screw 150 to repair the failed metatarsophalangeal joint of FIG. 1. FIG. 3 illustrates a more detailed isometric view of bone plate 100. For reference purposes, bone plate 100 and its various features may be referred to as having a top surface intended to face away from the bones of joint 106 and a bottom surface intended to face toward the bones of joint 106 (e.g., to be placed upon the bones of joint 106). Though particular features of bone plate 100 may be explained using such intended placement as a point of reference, this method of explanation is not meant to limit the scope of the present disclosure to any particular configuration or orientation of bone plate 100.

As shown in FIG. 2, bone plate 100 is being used to reconstruct a failed joint 106 of a human foot. In particular, FIG. 2 illustrates transfixation screw 150 being inserted through bone plate 100 into a first bone 104a and a second bone 104b (collectively, bones 104) in order to fuse joint 106 (show collapsed in FIG. 1). Bone 104a refers to the bone positioned directly beneath transfixation screw hole 102 (e.g., touching the bottom surface of transfixation screw hole 102) while bone 104b refers to the bone positioned on the opposite side of joint 106. Although bone 104a is illustrated and described as the first metatarsal, bone 104b is illustrated and described as the first proximal phalanx, and joint 106 is illustrated and described as the metatarso-phalangeal joint 106 of the big toe, one of ordinary skill in the art will appreciate those specific examples are presented for the sake of explanatory clarification and will further appreciate that bones 104 and joint 106 may generically refer to any suitable set of bones forming any suitable joint in the body.

In a typical procedure, a surgeon may use bone plate 100 to fuse joint 106 according to the following example surgical procedure. To begin the procedure, the surgeon may create an incision over joint 106 to expose bones 104. After exposing bones 104, the surgeon may perform any pre-fusion steps such as removing cartilage from joint 106 and reducing the opposing faces of bones 104 to a bleeding bone bed. Following the pre-fusion steps, the surgeon may approximate bones 104 by positioning them next to one in a desired configuration for fusion. The surgeon may then secure bones 104 together by placing bone plate 100 across joint 106 such that transfixation screw hole 102 overlies bone 104a. The surgeon may screw bone plate 100 to bones 104, for example by inserting one or more bone screws 134 into one or more screw holes located on either end of bone plate 100, after which, the surgeon may create a path for transfixation screw 150. To create a path for transfixation screw 150, the surgeon may drill a pilot hole into bones 104 through transfixation screw hole 102. In particular embodiments, the surgeon may use the central axis 116 of transfixation screw hole 102 as a guide to establish the trajectory for the pilot hole. Once the pilot hole has been created, transfixation screw 150 may be inserted into the pilot hole through transfixation screw hole 102 and screwed into bones 104 until the head of transfixation screw 150 abuts the inner surface of transfixation screw hole 102. After bones 104 have been secured together using transfixation screw 150, the surgeon may close the incision, leaving bones 104 to fuse together.

To facilitate the process of aligning bones 104, bone plate 100 may include one or more joint-specific characteristics that may conform to the natural geometry of joint 106 or bones 104. For example, in the case of the metatarso-phalangeal joint, bone plate 100 may include a rise (similar to rise 210 in FIG. 4) that fits over the head on the dorsal section of metatarsal 104a. This may enable bone plate 100 to be seated firmly against the head of metatarsal 104a and provide a natural footing for bone plate 100 against metatarsal 104a. In other embodiments, the rise may be eliminated from bone plate 100 and the dorsal head of metatarsal 104a may be ground down to enable bone plate 100 to be laid flush against bones 104.

Depending upon design, bone plate 100 may further include a dorsiflexion angle (of approximately 10 degrees) between the first end 126b of the plate and the second end 126a of the plate that mimics the natural elevation of the first metatarsal 104a relative to the first proximal phalanx 104b. The inclusion of a dorsiflexion angle between first end 126b and second end 126a may reduce the force on bone plate 100 during activities such as walking. Furthermore, bone plate 100 may include a valgus angle (of approximately 10 degrees) between the first end 126b of the plate and the second end 126a of the plate that mimics the natural lateral alignment of the first metatarsal 104a relative to the first proximal phalanx 104b. The inclusion of a valgus angle in bone plate 100 may further help to reduce the force on bone plate 100 during activities such as walking. In particular embodiments, to provide lateral support for joint 106, the ends of plate 100 may be may be curved around the medial side of bones 104. One of ordinary skill in the art will appreciate that above-described characteristics of bone plate 100 were described with respect to the metatarso-phalangeal joint for the sake of explanatory simplicity and will further appreciate that particular embodiments of bone plate 100 may be adapted equally as well to approximate the natural geometry of virtually any joint 106 in the body without departing from the scope of the present disclosure.

As mentioned above, transfixation screw 150, once inserted across joint 106, may absorb a portion of the stress that would otherwise be exerted on the portion of bone plate 100 spanning across joint 106 when a load is placed upon joint 106. For example, in the case of the metatarso-phalangeal joint 106, activities that place weight on the foot, such as walking or standing, may cause metatarso-phalangeal joint 106 to flex. Due to the biomechanics of the foot, when the metatarso-phalangeal joint 106 flexes, the upper or "dorsal" side of joint 106 will compress together, while the bottom or "plantar" side of joint 106 will draw apart under tension. This is generally true for any hinge-type joint. The line about which the force on joint 106 transitions from tension to compression may be referred to as the neutral bending axis 118 of the joint 106. In other words, neutral bending axis 118 defines the boundary line that separates the tension side of joint 106 from the compression side of joint 106.

When transfixation screw 150 is screwed into joint 106 along a trajectory that crosses neutral bending axis 118 (as show in FIG. 2), a "tension band" construct is created that puts transfixation screw 150 under tension when joint 106 flexes. Normally, the plantar side of bone 104a (e.g., the portion of bone 104a on the tension side of joint 106) will draw away from the plantar side of bone 104b when a load is applied to joint 106. However, when transfixation screw 150 is screwed across joint 106 such that the head 152 of transfixation screw 150 abuts the inner surface of transfixation screw hole 102, the portion of transfixation screw 150 engaged with bone 104b will pull against the head 152 of transfixation screw 150 when a load is applied to joint 106. Since the head of transfixation screw 150 is braced against the inner surface of transfixation screw hole 102, it will absorb the tension forces transmitted up the shaft of transfixation screw 150, preventing the plantar side of bone 104b from drawing away from the plantar side of bone 104a.

In particular embodiments, the interface between bone 104a and transfixation screw 150 may provide another mechanism for absorbing the tension forces transmitted up the shaft of transfixation screw 150. For example, if transfixation screw 150 is threadably engaged with bone 104a, the threading on transfixation screw 150 may provide a footing against bone 104a which may also absorb a portion of the tension forces transmitted up the shaft of transfixation screw 150 from bone 104b when a load is applied to joint 106. In either case, once transfixation screw 150 has been screwed into joint 106 along a trajectory that crosses the neutral bending axis 118 of joint 106, a tension band construct may be created that enables transfixation screw 150 to absorb the tension forces that would otherwise draw the tension side of joint 106 apart when a load is placed on joint 106.

In particular embodiments, transfixation screw hole 102 may be used to establish the trajectory for transfixation screw 150. For example, bone plate 100 may be configured such that, once bones 104 have been approximated and bone plate 100 has been placed across joint 106, the central axis 116 of transfixation screw hole 102 may align along a trajectory that crosses the neutral bending axis 118 of joint 106. For example, the central axis 116 of transfixation screw hole 102 may be configured to pass through joint 106 at a transfixation angle 114 of about 30 degrees to about 70 degrees relative to neutral bending axis 118 to achieve the desired tension band construct once bone plate 100 is secured across joint 106. In one example embodiment, central axis 116 may be configured to pass through joint 106 at a transfixation angle 114 of about 50 degrees. Consequently, by drilling a pilot hole along central axis 116, a surgeon may create a path for transfixation screw 150 that spans from a first position 120 on bone 104a located on the compression side of joint 106 to a second position 122 on bone 104b located on the tension side of joint 106, creating the desired tension band construct for transfixation screw 150. Alternatively, a surgeon may forgo drilling a pilot hole and may instead use a transfixation screw 150 having a self drilling feature. In that case, the surgeon could achieve a tension band construct by screwing the transfixation screw 150 directly into joint 106 along the trajectory of central axis 116.

Transfixation screw 150 may be any component of hardware having a head 152 configured to abut the surface of bone plate 100 and a shaft 154 operable to secure bones 104 together in a fixed configuration. For example, transfixation screw 150 may be a nut and bolt assembly, a pin assembly, or a bone screw. As another example and not by way of limitation, transfixation screw 150 may be a lag screw that includes a head 152 coupled to a shaft 154 having an unthreaded portion 156 and a threaded portion 158 that ends at a tip 156. Once transfixation screw 150 is screwed into bones 104 through transfixation screw hole 102, this configuration of transfixation screw 150 may result in a lag effect that may tighten the interface between bones 104 when transfixation 150 is rotated. In particular embodiments, the length of shaft 154 may be less than the length of the portion of central axis 116 that passes through bones 104 in order to keep tip 156 from protruding out of bone 104b (e.g., out of the plantar aspect of first proximal phalanx 104b) when transfixation screw 150 screwed into bones 104.

To achieve a lag effect, a surgeon, after affixing bone plate 100 across joint 106 and drilling a pilot hole for transfixation screw 150 as described above, may screw transfixation screw 150 into joint 106 until unthreaded portion 156 extends completely through bone 104a and threaded portion 158 threadably engages bone 104b. At this point, further rotation of transfixation screw 150 may cause threaded portion 158 to advance further into bone 104b, causing bone 104b to ride up further onto shaft 154 and press against bone 104a while unthreaded portion 156 spins freely within bone 104a. Transfixation screw 150 may be further rotated under these conditions until head 152 conies to bear on the inner surface of transfixation screw hole 102, cinching bone 104a between the bottom surface of bone plate 100 and bone 104b. This may create a tight interface between bones 104, increasing the chance of a positive fusion. In another example procedure, a lag effect may be achieved by drilling a pilot hole in bone 104a that is larger in diameter than shaft 154. This may enable transfixation screw 150 to spin freely within bone 104a to achieve the desired lag effect, even if the entirety of shaft 154 is threaded.

FIG. 3 illustrates an external view of the top surface of bone plate 100. In particular embodiments, bone plate 100 may be characterized by a substantially thin construction that generally includes an elongate spine 124 having a first end 126a that includes at least one attachment point 128 for attaching first end 126a to bone 104a, a second end 126b comprising at least one attachment point 128 for attaching second end 126b to bone 104b, and a bridge portion 130 disposed between ends 126 configured to span across joint 106. Bone plate 100 may further include a transfixation screw hole 102, and a compression hole 132 which may be used to cinch bones 104 together using a bone screw 134.

Each attachment point 128 may be any mechanism or fixture operable to serve as a rigid point of attachment between bone plate 100 and a bone 104. As one example and not by way of limitation, an attachment point 128 may be an unthreaded screw hole in bone plate 100 configured to accept a bone screw 134. As another example and not by way of limitation, an attachment point 128 may be a threaded screw hole that provides a locking interface between bone screw 134 and bone plate 100. To accomplish this locking interface, the underside of the head of screw 134 may include threads that interfere with the threading on the inside of the threaded screw hole to lock bone screw 134 into bone plate 100. Consequently, once bone screw 134 is screwed into bone 104 through the threaded screw hole, bone screw 134 may be prevented from loosening or backing out of bone 104. An example system for providing a locking interface between a screw hole and a screw is presented in U.S. Provisional Application No. 61/106,511, entitled, "Angulated Locking Plate/Screw Interface." In particular embodiments, the inner surface of transfixation screw hole 102 may also be threaded to provide a locking interface between transfixation screw 150 and bone plate 100. In this case, the head of transfixation screw 150 may also be threaded.

As another example and not by way of limitation, an attachment point 128 may be any type of clip or clamp included on bone plate 100 operable to rigidly affix bone plate 100 to a bone. One of ordinary skill in the art will appreciate that the above-described embodiments of attachment points 128 were presented for the sake of explanatory clarification and will further appreciate that the present disclosure contemplates each attachment point 128 being any suitable mechanism or fixture operable to serve as a rigid point of attachment between bone plate 100 and bone 104.

Spine 124 may generally define the central portion of bone plate 100 spanning along the length of bone plate 100. As an example and not by way of limitation, spine 124 may include a contiguous linear or curvilinear section of bone plate 100 spanning from the tip of first end 126a to the tip of second end 126b. As mentioned above, spine 124 includes a bridge portion 130 configured to span across joint 106. Since bridge portion 130 is configured to span across joint 106, it is typically defined by an unbroken section of spine 124 that is free of voids such as positioning holes or screw holes that could potentially reduce the bending strength of bridge portion 130. Depending upon design, bridge portion 130 may include a thickened section 136 of bone plate 100 to increase the bending strength of bridge portion 130. This may lessen the risk of bridge portion 130 bending or breaking above joint 106 when a load is applied to joint 106.

In particular embodiments, thickened section 136 may be defined by a thickened ridge of material in hone plate 100 having its greatest thickness along bridge portion 130 and gradually decreasing in thickness as one moves away from bridge portion 130 along the length of bone plate 100 toward ends 126. The increased material thickness may provide central section 130 with a higher section modulus than the proximal and distal areas of the plate located at ends 126. In a typical design, thickened section 136 may be about 100% to 200% thicker than the adjacent portions of bone plate 100. Including thickened section 136 in bone plate 100 may confer a number of advantages over plates of uniform thickness, one of which is the ability to efficiently increase the section modulus (and strength) of bridge portion 130 without adding material thickness to the entirety of bone plate 100.

Transfixation screw hole 102 may be defined by an inner surface of bone plate 100 surrounding a generally circular opening in bone plate 100, As an example and not by way of limitation, transfixation screw hole 102 may be disposed along the center line 138 of spine 124, immediately adjacent to bridge portion 130. In the case of a bone plate 100 designed for use on the first metatarso-phalangeal joint, the placement of transfixation screw hole 102 adjacent to bridge portion 130 may enable transfixation screw 102 to penetrate the first metatarsal 104a on the dorsal aspect of the metatarsal head and pass into the plantar cortex of the first medial phalanx 104b, transfixing the metatarso-phalangeal joint 106.

In particular embodiments, the portion of bone plate 100 that includes transfixation screw hole 102 may be thicker than other portions of hone plate 100. For example, transfixation screw hole 102 may be included in thickened section 136, adjacent to bridge portion 130. This may enable a countersink to be created around transfixation screw hole 102 so that the head 152 of transfixation screw 150 may rest flush with the top surface of bone plate 100 once transfixation screw 150 is screwed into transfixation screw hole 102. The increased plate thickness around transfixation screw hole 102 may also enable transfixation screw hole 102 to be machined into bone plate 100 at an angle relative to the top surface of bone plate 100 (e.g., other than perpendicular to the top surface of bone plate 100).

As mentioned above, in particular embodiments, bone plate 100 may include a compression hole 132 for tightening bones 104 together using a bone screw 134. Compression hole 132 may be defined by an inner surface of bone plate 100 surrounding a generally oblong opening in bone plate 100. More particularly, the inner surface of compression hole 132 may have a narrow end 131a, and a wide end 131b that includes a horse-shoe-shaped countersink 133. To compress bones 104 together using compression hole 132, a surgeon may use the following example procedure. The surgeon may begin by attaching the second end 126b of bone plate 100 to bone 104b using the attachment points 128 located on end 126b. The surgeon may then manually approximate bone 104a against bone 104b, placing bone 104a under compression hole 132. While holding bone 104a against the bottom surface of compression hole 132, either by hand or using a clamp, the surgeon may drill a pilot hole for bone screw 134 into bone 104a. The trajectory of the pilot hole may be generally perpendicular to the top surface of bone plate 100 and be located approximately in the center of narrow end 131a (e.g., located at the focus of narrow end 131a).

After creating the pilot hole, the surgeon may then screw bone screw 134 into the pilot hole until the head of bone screw 134 comes into contact with countersink 133 near the tips 135 of countersink 133. To facilitate the compression feature, the underside of the head of bone screw 134 may be generally conical, having a taper angle approximately equal to the taper angle of countersink 133. Once the head of bone screw 135 is in contact with counter sink 133 near tips 135, further rotation of bone screw 135 may cause the head of bone screw 134 to ride down into countersink 133, drawing bone plate 100 further up onto bone 104a and causing bones 104 to press together at the interface of joint 106. After approximating bones 104 by screwing bone screw 134 into compression hole 132 as just described, the surgeon may use other attachment points 128 to further secure bone plate 100 to bone 104a. The surgeon may also screw transfixation screw 150 into joint 106 through transfixation screw hole 102 after tightening bones 104 together using compression hole 132. Depending upon design, compression hole 132 may be threaded to provide a locking interface for bone screw 134.

In particular embodiments, bone plate 100 may comprise one or more positioning holes 140 that may be used to position bone plate 100 relative to the bones 104 of joint 106. To position bone plate 100 using a positioning hole 140, a surgeon may insert a K-wire into one of the bones 104, after which the surgeon may position bone plate 100 on bone 104 by inserting the K-wire through positioning hole 140 and sliding bone plate 100 down onto bone 104. Additionally, the surgeon may rotate bone plate 100 about the K-wire using positioning hole 140 to achieve a desired orientation of bone plate 100 relative to bone 104. To ensure that bone plate 100 may be precisely positioned on bone 104 using a K-wire, the diameter of positioning hole 140 may be approximately equal to the diameter of the K-wire. Once bone plate 100 has been properly positioned, the surgeon may secure bone plate 100 to bone 104, temporarily for example, by inserting another K-wire into another one of positioning holes 140, or more permanently, using attachment points 128.

In particular embodiments, the bottom surface of bone plate 100 may include one or more contact reduction features 146 which may reduce the amount of surface area of bone plate 100 that contacts bones 104 when bone plate 100 is secured across joint 106. As an example and not by way of limitation, the bottom surface of bone plate 100 may include one or more channels, notches, or other recessions which may reduce (e.g., minimize) the amount of bone plate 100 that contacts bones 104. This may lessen the amount of vascular impingement caused by bone plate 100, promoting blood flow to bones 104 and bone growth. In particular embodiments, each of the screw holes in bone plate 100 (e.g., attachment points 128, compression hole 132, or transfixation screw hole 102) may include a countersink capable of seating the head of a screw flush with the top surface of bone plate 100. This feature may provide several benefits such as lessening the chance of uncomfortable impingement on the surrounding soft tissue, and reducing patient palpation and visualization of bone plate 100.

In particular embodiments, bone plate 100 may further include flared hips 148 adjacent to transfixation screw hole 102. Flared hips may generally be defined by a widened section of bone plate 100. As an example and not by way of limitation, flared hips 148 may include two generally parabolic wings extending laterally from spine 124, symmetrically opposed to one another about transfixation screw hole 102. As will be appreciated by one of skill in the art, the entry point for transfixation screw 150 into bone 104a may be generally be located at the center of the bottom side of transfixation screw hole 102 when transfixation screw is inserted into transfixation screw hole 102 along central axis 116. Consequently, in embodiments where transfixation screw hole 102 is formed into bone plate 100 at an angle, the entry point for transfixation screw 150 may be out of sight (e.g., covered up by the top of transfixation screw hole 102) when bone plate 100 is viewed from above. Therefore, to help a surgeon precisely position the entry point for transfixation screw 150 onto a desired location on bone 104a, the entry point for transfixation screw 150 (e.g., the center of the bottom side of transfixation screw hole 102) may reside directly in between the widest portion of flared hips 148. Accordingly, by positioning the widest portion of hips 148 directly adjacent to the desired location for transfixation screw 150 on bone 104a, the surgeon may confidently position the entry point for transfixation screw 150 at the desired location, even when the entry point is out of sight. Flared hips 148 may also increase the strength of bone plate 100 around transfixation screw hole 102, lessening the chance of plate deformation or breakage.

Depending upon design, bone plate 100 may be formed from any material or combination of materials suitable for forming medical implants. Such materials may have high strength-to-weight ratios and may be inert to human body fluids. As an example and not by way of limitation, bone plate 100 may be formed from a forged titanium alloy.

Titanium may provide several benefits as a material for bone plate 100 such as being relatively lightweight, providing adequate strength for withstanding forces typically experienced by a bone plate, and being visible in radiographs of the implant region.

Figure 4:
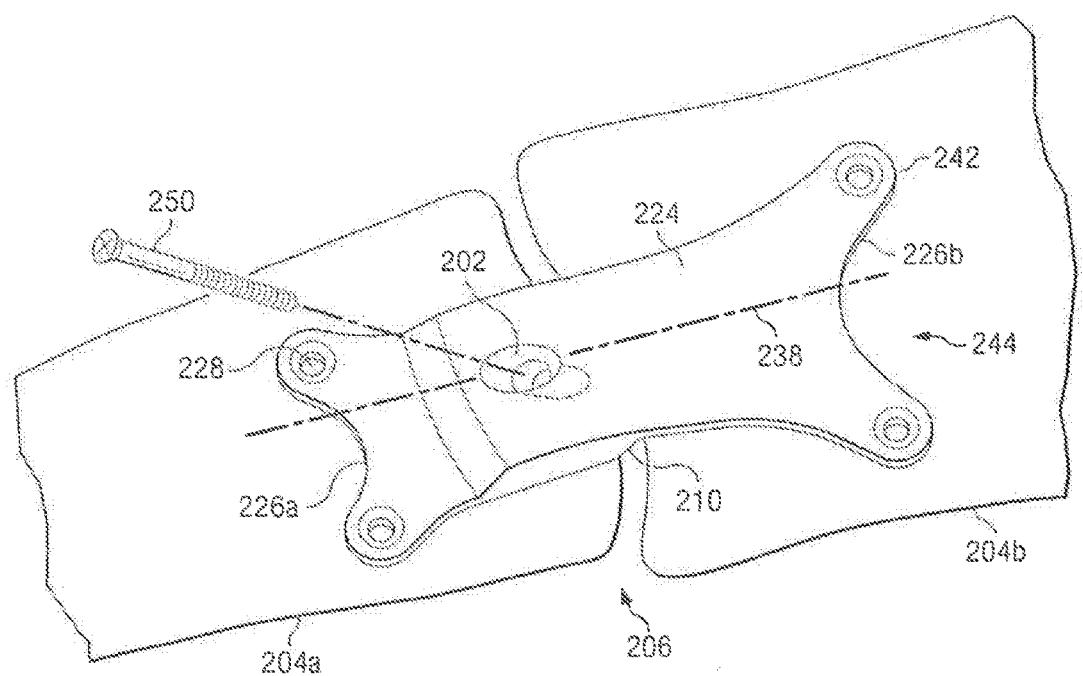
FIG. 4 illustrates a bone plate adapted for use on a tarso-metatarsal joint according to an example embodiment of the present disclosure.

FIG. 4 illustrates an example embodiment of a bone plate 200 adapted for use in a Lapidus procedure where bone plate 200 may be secured across the first tarso-metatarsal (TMT) joint 206, located between the first metatarsal 204a and the first cuneiform 204b. Though bone plate 200 is adapted for placement over the TMT joint, particular embodiments of bone plate 200 may include some or all of the features of bone plate 100 described above, appropriately adapted to conform to the TMT joint 206. For example, when used on TMT joint 206, transfixation screw hole 202 may be configured to guide a transfixation screw 250 from the dorsal aspect of metatarsal 204a to the plantar aspect of first cuneiform 204b in order to transfix TMT joint 206. Likewise, bone plate 100 may include some or all of the features described with respect to bone plate 200, appropriately adapted to conform to the MPJ joint 106. For reference purposes, like numbers may be used to refer to like features between bone plate 100 and bone plate 200.

Bone plate 200 may generally be "H-shaped", and include an elongate spine 224 having a plurality of flanges 242 extending laterally therefrom. Each flange 242 may further include one or more attachment points 228 (similar or identical to attachment points 128 described above) for attaching bone plate 200 to a bone 204. Flanges 242 may serve as a primary mechanism for attaching bone plate 200 to bones 204, although particular embodiments of bone plate 200 may further include one or more additional attachment points 228 disposed along spine 224 for attaching bone plate 200 to bones 204.

Each flange 242 may be any type of rigid lateral extension from spine 224. As an example and not by way of limitation, each flange 242 may be a rigid rounded tab extending laterally from the side of spine 224. Depending upon design, each flange 242 may be separated from the next by a gap 244, which may enable a surgeon to independently contour each flange 242 to a desired position (e.g., to conform flanges 242 to match the geometry of bones 204). Furthermore, each flange 242 may be relatively thinner than spine 224 to reduce the mechanical force needed to contour flanges 242 up or down relative to spine 224. This thinning of flanges 242 may confer a number of advantages over plates having uniform thickness, such as for example, providing a surgeon with the ability to easily contour flanges 242 to a desired position. In particular embodiments, flanges 242 may enable a surgeon to contour bone plate 200 such that attachments points 242 are located on both the medial and dorsal aspects of bones 204. Once a flange 242 has been contoured to a desired position, it may be affixed to bone 204 using an attachment point 228.

To facilitate the process of aligning bones 204, bone plate 200 may include one or more features which mimic the natural geometry of the TMT joint 206. For example, bone plate 200 may include a rise 210 of approximately 0 mm to 5 mm (e.g., 2 mm) that mimics the natural elevation of the first metatarsal 204a relative to the first cuneiform 204b. As another example and not by way of limitation, bone plate 200 may include a varus angle of about 0 degrees to about 30 degrees (e.g., 15 degrees) between the first end 226a of the plate and the second end 226b of the plate that mimics the natural elevation of first metatarsal 204a relative to first cuneiform 204b. in particular embodiments, bone plate 200 may be symmetric about center line 238 to enable bone plate 200 to be applied to either the left foot or the right foot, without substantial modification.

The particular embodiments disclosed above are illustrative only, as particular embodiments of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. In particular, every range of values (e.g., "from about a to about b," or, equivalently, "from approximately a to b," or, equivalently, "from approximately a-b") disclosed herein is to be understood as referring to the power set (the set of all subsets) of the respective range of values. The terms in the claims have their plain, ordinary meaning unless otherwise explicitly and clearly defined by the patentee.

Although the present disclosure has been described in several embodiments, a myriad of changes, substitutions, and modifications may be suggested to one skilled in the art, and it is intended that the present disclosure encompass such changes, substitutions, and modifications as fall within the scope of the present appended claims.

What is claimed is:

1. A system for securing a first discrete bone and a second discrete bone together across a joint between the first discrete bone and the second discrete bone, the system comprising:
   a plate comprising:
      an elongate spine having a first end comprising at least one attachment point for attaching the first end to the first discrete bone on a first side of the joint, a second end comprising at least one attachment point for attaching the second end to the second discrete bone on a second side of the joint, and a bridge portion disposed between the first end and the second end, the bridge portion having a portion configured to span across the joint, the bridge portion further comprising a thickened portion having a thickness greater than at least a portion of a thickness of either the first end or the second end; and
      an aperture defining a transfixation screw hole disposed along the spine at the thickened portion of the bridge portion, the transfixation screw hole comprising an inner surface configured to direct a transfixation screw through the transfixation screw hole such that the transfixation screw extends at a trajectory configured to pass through a first position on the first discrete bone and a second position on the second discrete bone once the plate is placed across the joint.

2. The system of claim 1, further comprising a transfixation screw, said transfixation screw comprising a head configured to abut the inner surface of the transfixation screw hole and a shaft configured to contiguously extend through the first discrete bone, across the joint, and into the second discrete bone.

3. The system of claim 2, wherein the transfixation screw comprises a lag screw having:
   at a first end of the shaft adjacent to the head, an unthreaded portion configured to extend through the first discrete bone; and
   at a second end of the shaft adjacent to a tip of the transfixation screw, a threaded portion configured to extend into the second discrete bone.

4. The system of claim 1, wherein the inner surface of the transfixation screw hole is configured to lockably engage a head of a transfixation screw.

5. The system of claim 4, wherein the inner surface of the transfixation screw hole is threaded to provide a locking interface with a transfixation screw.

6. The system of claim 1, wherein the first position resides on a compression side of the joint and the second position resides on a tension side of the joint.

7. The system of claim 1 wherein the plate is configured to substantially conform to a geometry of the respective first and second discrete bones on which the plate is configured to be disposed.

8. The system of claim 1, wherein:
a central axis of the inner surface of the transfixation screw hole defines the trajectory; and
the trajectory is configured to cross a neutral bending axis of the joint once the plate is placed across the joint.

9. The system of claim 8 wherein the trajectory is configured to pass through the joint at a transfixation angle between about 30 degrees and about 70 degrees measured from the neutral bending axis.

\* \* \* \* \*